Figure 1:
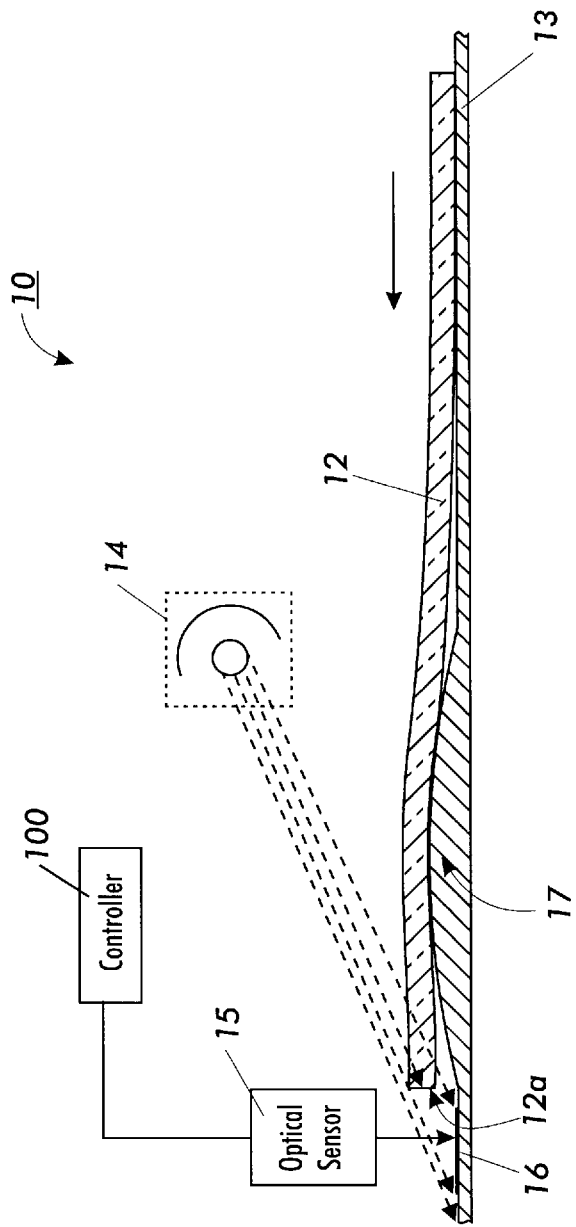

United States Patent
Acquaviva

[19]
[11] Patent Number: 5,859,440
[45] Date of Patent: Jan. 12, 1999

[54] TRANSPARENCY SHEET EDGE DETECTOR SYSTEM USING EDGE SHADOW SENSING

[75] Inventor: Thomas Acquaviva, Penfield, N.Y.

[73] Assignee: Xerox Corporation, Stamford, Conn.

[21] Appl. No.: 923,587

[22] Filed: Sep. 4, 1997

[51] Int. Cl.[6] ................................................ G01N 21/86
[52] U.S. Cl. .................................. 250/559.36; 250/223 R
[58] Field of Search .......................... 250/559.36, 223 R, 250/559.24, 559.25; 356/384, 385, 386

[56] References Cited

U.S. PATENT DOCUMENTS

| | | | |
|---|---|---|---|
| 4,417,148 | 11/1983 | Otake ................................... | 250/559.36 |
| 4,540,887 | 9/1985 | Minerd et al. .......................... | 250/561 |
| 5,075,543 | 12/1991 | Courtney ............................... | 250/223 R |
| 5,139,339 | 8/1992 | Courtney et al. ....................... | 356/446 |
| 5,280,171 | 1/1994 | Halter .................................... | 250/223 R |
| 5,309,515 | 5/1994 | Troung et al. ........................ | 250/559.24 |
| 5,329,338 | 7/1994 | Merz et al. ............................. | 355/207 |
| 5,521,692 | 5/1996 | Bares ...................................... | 335/311 |

*Primary Examiner*—Edward P. Westin
*Assistant Examiner*—Kevin Pyo

[57] ABSTRACT

A dual mode non-contact optical sheet edge detection system for detecting either fully transparent or regular sheets being fed in a sheet transport path of a reproduction system, with an illumination source for illuminating the potential sheet edge area at an angle to generate a detectable sheet edge shadow from transparent sheets, and an optical detection system remotely detecting the generated edge shadow to provide sheet edge location or timing information to a control system. Preferably the sheet edge is held spaced above the illuminated sensor an illuminated sensor target area to enhance the shadow effect.

8 Claims, 2 Drawing Sheets

TRANSPARENCY SHEET EDGE DETECTOR SYSTEM USING EDGE SHADOW SENSING

Cross-reference is made to a contemporaneously filed application on sheet edge shadow sheet edge position detection in document feeder sheet stacks or reproduction machine output sheet stacks by this same inventor together with Jan Bares, and the same assignee, entitled "Size or Position Sensing of Intermixed Sheets in a Sheet Stacking Tray with Sheet Edge Shadow Detection", App. Ser. No. 08/923,588, Attorney Docket No. D/96728.

The embodiments herein disclose a system for the detection of the position of at least one edge of a transparent image substrate sheet in a sheet transport system such as the paper path or document feeding path of an image reproduction apparatus by a non-contacting optical detection system detecting a generated edge shadow of the transparent sheet. This detected information may be variously utilized, such as for control of the associated imaging or printing system. A dual mode system is disclosed which is fully compatible with detection of ordinary non-transparent paper substrate sheets at the same reproduction machine path locations by the same sensors as well as fully transparent sheets.

By way of background, it is noted that the optical detection of transparencies, especially those being fed into and through the paper path of xerographic and other reproduction systems to be printed, is a particularly difficult problem. Conventional machine paper path optical sensors typically detect the edges of substrates passing through various particular locations in such machines by the occlusion of light by essential opaque normal paper substrate material. These sensors look for a change in the amount of transmitted or reflected light reaching the optical sensor. In this manner, they can detect the lead and trail edge of a sheet, or its side edge location. Transparencies, of course, by definition and nature do not block or restrict little of the light reaching the sensor. Also, transparencies are often slipperier, stiffer, or otherwise harder to feed and thus more misfeeding and jam prone, and thus especially need paper path sensor detection for location timing for misfeeding or jam detection. Thus, traditionally, many reproduction machines require the use of transparencies which have peelable paper strips, printed white stripes, or are backed by white sheets of paper, which will trigger these sensors, in order to allow reliable transparency feeding. These special transparency sheets for copiers or printers are widely commercially available, and need not be described herein. However, a white stripe at one edge wastes usable imaging space on the transparency sheet, and only allows that one edge to be detected by a conventional sensor, and typically must be loaded in a particular orientation. Paper backed transparencies are also difficult to handle because they must be loaded in a two axis restricted particular orientation, and are expensive. Likewise, many document handlers or document feeders, as they are interchangeably called, cannot reliably feed transparent originals to be electronically or optically scanned or otherwise reproduced through their document feeding and imaging paths.

Disclosed herein is a novel dual mode optical sensing system which can detect any edge of a true transparency as it moves in a reproduction system sheet path. That is, edge detection of a non-striped, non-backed, completely transparent transparency substrate sheet. Yet, this same system also detects non-transparency material such as ordinary paper sheets in the same locations with the same sensor.

Further by way of background, the general use of reflective or transmitting optical detection systems for detecting the edge of a document sheet in a reproduction apparatus such as a copier, printer or scanner is well known. One example, with angled illumination, is Xerox Corporation U.S. Pat. No. 4,540,887 issued Sep. 10, 1985 to T. M. Minerd, et al. Other sensors are cited therein. Another reproduction machine paper path optical sheet sensor with angled illumination is shown in Xerox Corporation U.S. Pat. No. 5,075,543 issued Dec. 24, 1991 to John E. Courtney.

Of particular interest here, Xerox Corporation U.S. Pat. No. 5,139,339 discloses a substrate media discriminating and presence sensor that can detect and discriminate between paper and transparencies using a light emitting diode and two detectors configured to measure both diffuse and specular reflectivity of the media. (Typically, paper reflects light more diffusely and transparencies reflect light more specularly, due to surface roughness differences.) These measurements are used to discriminate between the two types of copy sheets in this reference.

Also relevant to optical detection of transparency sheets is U.S. Pat. No. 5,329,338, which, according to a characterization in another application, teaches detecting and discriminating a copy sheet in an electronic reprographic printing system. A diffuse reflective sensor is located adjacent to the path over which the copy sheet moves. The sensor is disposed so that its optical axis intersects the copy sheet where the angle of intersection between the copy sheet and the optical axis remains within a specified range of angles for the maximum length of the copy sheet. Another jam detection sensor is disposed along inlet baffles of a paper path and is used to detect both opaque and transparent copy sheets. A distinguishing sensor is also disposed adjacent copy sheet inlet baffles with its optical axis aligned so that a transparent copy sheet is not detected, while an opaque copy sheet is detected.

Also of interest, Xerox Corporation U.S. Pat. No. 5,521,692 issued May 28, 1996 to Jan Bares suggests identifying surface relief features of a substrate in a printing machine by apparatus including a very low, grazing angle light source illumination of the surface to receive signals of ridges and depressions in the substrate surface indicating surface relief features of the substrate.

The present system may be utilized with various different reproduction systems and paper paths, known from the above and various other references and products, and thus need not be described in detail herein. That can also include document feeders or document handlers for feeding documents to be imaged, since such documents may also sometimes include transparencies. For example, in a document handler, typically the lead edge of a document is detected as it is fed downstream by occlusion by that moving sheet lead edge of a conventional lead edge detector near the entrance of the document handler, such as sensor 31 in Xerox Corp. U.S. Pat. No. 5,596,399.

In the present system it has been found that by appropriately angled illumination, appropriate positioning or spacing of the transparency from a sensor target surface or sensor, and appropriate detection, that an edge shadow can be generated and detected even of the thin edges of fully transparent sheets passing through a reproduction apparatus.

A specific feature of the specific embodiments disclosed herein is to provide a dual mode non-contact optical sheet detection system for detecting at least one sheet edge of either fully transparent or opaque paper image substrate sheets in a sheet transport path of an image reproduction apparatus, comprising an illumination source for illuminating the surface of either a transparent or opaque sheet moving in said sheet transport path at a sufficiently shallow illumination angle to the surface of said sheet to generate a detectable edge shadow directly adjacent to said sheet edge from either a transparent or opaque, said illumination angle being substantially greater than a grazing angle to not form shadows from said surface of said sheet; and an optical detection system positioned to remotely detect in said sheet transport path said detectable edge shadow of said sheet without contacting said sheet; said optical detection system providing a control signal corresponding to said sheet edge passing said optical detection system.

Further specific features disclosed herein, individually or in combination, include those wherein said illumination source illuminates an optical target area on one side of said sheet transport path, and said optical detection system comprises a photodetecter on the opposing side of said sheet transport path optically aimed at said target area; and/or further including a spacer associated with said sheet transport path for spacing said sheet edge from said optical target area to enhance said generated edge shadow; and/or wherein said optical target area is an optically reflective matte finish surface; and/or wherein said optical detection system is positioned on the opposite side of said sheet transport path from said illumination source to be directly illuminated by said illumination source, and positioned to detect a lateral extent of a sheet moving orthogonally thereto in said sheet transport path; and/or, wherein said optical detection system comprises a low resolution multiple photodetector array bar positioned at one said sheet transport path for the actuation of one or more respective said photodetectors by an edge shadow of a lateral sheet edge in said sheet transport path; and/or wherein said optical detection system comprises a low resolution photodetector array bar with an optical resolution of only approximately 3 mm or greater; and/or wherein said illumination source illuminates a sheet in said sheet transport path with a said illumination angle of approximately 15 degrees to the surface of the sheet; and/or wherein said sheet transport path includes lifting means for lifting a sheet in said sheet transport path by approximately 1 mm relative to said optical detection system to enhance said sheet edge shadow.

The disclosed system may be operated and controlled by appropriate operation of conventional control systems. It is well known and preferable to program and execute imaging, printing, paper handling, and other control functions and logic with software instructions for conventional or general purpose microprocessors, as taught by numerous prior patents and commercial products. Such programming or software may of course vary depending on the particular functions, software type, and microprocessor or other computer system utilized, but will be available to, or readily programmable without undue experimentation from, functional descriptions, such as those provided herein, and/or prior knowledge of functions which are conventional, together with general knowledge in the software and computer arts. Alternatively, the disclosed control system or method may be implemented partially or fully in hardware, using standard logic circuits or single chip VLSI designs. Likewise, various possible useful control functions of copiers and printers provided with sheet sizes and/or positions information is well known in the art and patent literature and need not be repeated here.

In the description herein the term "sheet", "document" or "original" refers to a thin and usually flimsy physical sheet of paper, plastic, or other suitable physical substrate for images. Transparencies are, of course, clear plastic such sheets.

As to specific components of the subject apparatus, or alternatives therefor, it will be appreciated that, as is normally the case, some such components are known per se in other apparatus or applications which may be additionally or alternatively used herein, including those from art cited herein. All references cited in this specification, and their references, are incorporated by reference herein where appropriate for appropriate teachings of additional or alternative details, features, and/or technical background. What is well known to those skilled in the art need not be described here.

Figure 2:
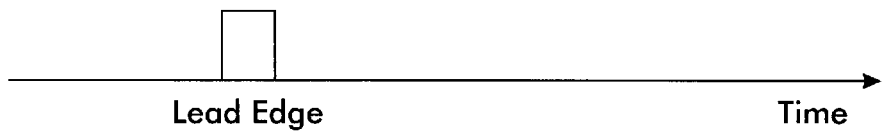
Figure 3:
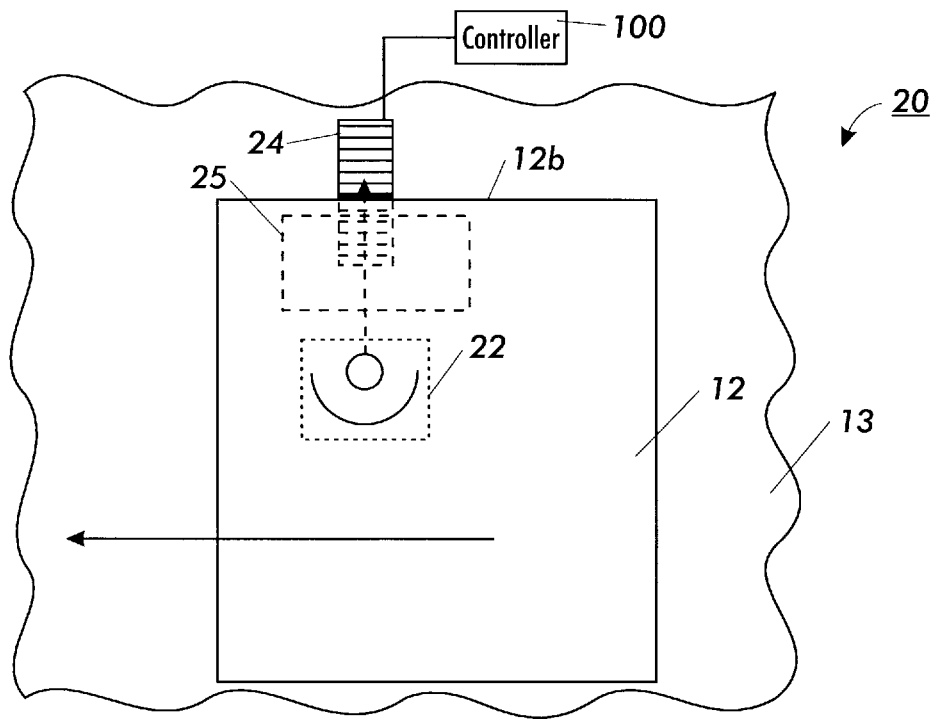
Figure 4:
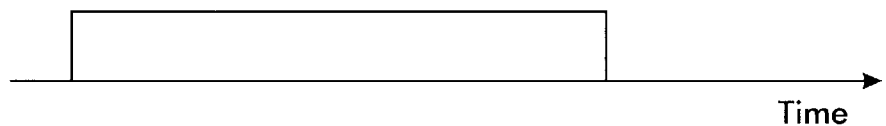

Various of the above-mentioned and further features and advantages will be apparent from the specific apparatus and its operation described in the examples below, including the drawing figures (approximately to scale) wherein:

FIG. 1 schematically illustrates in a partial cross-sectional side view a first embodiment of the subject transparency sheet detection system, using edge shadow detection, in a portion of a sheet or document feeding path of an otherwise conventional reproduction apparatus, for detecting the sheet leading or trailing edge in its movement direction;

FIG. 2 is an exemplary schematic view of the sensor electrical signal output with time (or equivalent sheet movement distance) of the embodiment of FIG. 1;

FIG. 3 schematically illustrates a slightly different embodiment in which a transparency sheet edge detection system is provided for detecting the lateral (orthogonal) edge position of a sheet or document feeding through an otherwise conventional reproduction apparatus; and FIG. 4 is an exemplary schematic view of the sensor electrical signal output with time (or equivalent sheet movement distance) of the embodiment of FIG. 3.

Disclosed in both of the above-noted embodiments, i.e., the system 10 of FIGS. 1 and 2, and the system 20 of FIGS. 2 and 3, is a desirable purely optical, non-contacting, sheet edge detection system for detection of at least one edge of a transparency (or any other) sheet 12 moving in a portion of a reproduction machine sheet path 13. A low angle illumination source 14 in FIG. 1, or 22 in FIG. 3, projects glancing light across the surface of the substrate sheet 12 as the sheet edge (12a in FIG. 1 or 12b in FIG. 3) passes by the sensor 15 or 24 location in the sheet path 13, creating an edge shadow as the sheet passes under the optical sensor/detector 15 or 24. An angle of approximately 15 degrees between the light beam and the surface of the sheet has been found to be suitable.

The optical detector or photosensor 15 in FIG. 1 is aimed downwardly, as shown by the illustrated arrow, directly or substantially perpendicularly at a white matte finish illuminated target surface area 16, and distinguishes between the normal reflected light level from that illuminated surface 16 and the dark edge shadow seen by the photosensor 15 at that target area 16 when the sheet 12 edge 12a reaches that area. That is, the difference in reflected light from the target area 16 being illuminated by the illumination source 14 with no sheet present versus the amount of reflected light from that surface 16 when that same target area 16 surface is being shadowed by the sheet edge 12a just upstream of this target area. Note that, unlike art cited above, this is not a transparency surface specular reflection system. It does not depend on the illumination from source 14 being reflected away from target 16 by the horizontal upper surface of the sheet 12. It is believed that the phenomena involved here is a brief thin moving shadow due to internal light reflection by the vertical end surface of the transparency of the angular light source, creating a brief pulse signal output as shown in FIG. 2.

For a normal substantially opaque sheet in the same sheet transport path, the sensor 15 signal would also have the same timing start, for the same useful sheet lead edge position information for the controller 100, from an edge shadow of the sheet. i.e., a dark or off signal output from the sensor 15 as the sheet lead edge passes that same position. Thus, both types of sheets lead edges can be detected and signaled. For a typical matte white sheet, after the lead edge passed under the sensor 15 the sensor 15 signal would then go back on until the entire white opaque sheet has passed through the target area 16, since the illumination form the illumination source would be reflected from a white matte sheet surface.

However, to avoid false signals from dark image areas on a preprinted sheet, it is preferable to ignore, interrupt or block the sensor 15 output in the controller 100 after the sheet lead edge signal is received, i.e., for the time period of the sheet passage past the sensor 15 following the lead edge signal, or slightly longer. The sheet passage time period, as well as the normal time period between successive sheet feeds, is normally known, and available in the controller 100, from the known pre-fixed sheet transport path velocity and the selected or measured length, or maximum possible length, of the sheets being fed.

In both embodiments here the sheet edge 12*a* or 12*b* to be detected is desirably raised or held up slightly above the target area backing surface, by approximately one m.m., as particularly shown in FIG. 1. This has been found to enhance the size of the detectable edge shadow. As shown, this may be accomplished with a simple unobstructing smooth baffle or protrusion 17 or 25 in the paper path under the sheet 12, of a slightly higher level than the target area 16 in FIG. 1 or the horizontal sensor 24 plane in FIG. 3.

In the leading (or trailing) edge detector example of FIGS. 1 and 2 a single sensor 15 with a narrow field of view may be used. Its output signal duration with time as shown in FIG. 2 is a function of the speed of the sheet 12, the illumination angle, and the height of the transparency sheet edge above the sensor detection surface or backing material, as discussed immediately above. The latter two factors, as noted, increase the shadow area. The output signal may be used by the controller 100 here in various known manners, such as for misfeeding or jam detection, lead edge registration, sheet length measurement, etc.

In the sheet side edge detector system of FIGS. 3 and 4, a known sensor array 24 comprising a bar of multiple photodetecter cells is used as a sheet 12 side edge 12*b* position detector. In this embodiment, the angled illumination from the source 22 is aimed directly at the sensor 24, instead of at a target area viewed by the sensor. The sensor 24 signal can be used by the conventional connecting controller 100 for either sheet width detection or lateral registration control, for example. Or, to change the selection of copy sheets onto which the image of that sheet will be printed, and/or the printed image size, as is well known per se. The detector 24 may be a simple, conventional scanning array bar with multiple photodetecters, such as are commonly commercially available. It may be of relatively low resolution, e.g. as low as 3 mm per pixel, and thus lower cost, for the purposes here, since only the approximate position of the edge shadow needs to be detected. That is, the edge shadow detection system does not have to be an imaging quality scanning array. It need only roughly detect the contrast between the light normally directed against it by the light source 22 relative to the absence of light in the shadow formed at the edge of that sheet being detected. The movement of the shadow between the photodetecter elements of the array 24 may be conventionally electronically detected by the connecting controller 100. That controller 100 can then be connected to the reproduction system elements to be controlled for the control functions described above or otherwise.

In both embodiments the illumination is at an angle substantially above a grazing angle to the sheet surface such as not to form shadows from surface irregularities of the sheet and thus to only form a detectable shadow from the edge of the transparent sheet.

In one test example, a glancing light source was placed to shine light at 15 degrees to a transparency sheet surface. With the transparency lead edge raised only 1 mm above a white sheet of paper (providing an exemplary optical base or sensor target), a distinct edge shadow was created which would be clearly optical sensor detectable, as in the FIG. 1 embodiment.

If further signal processing such as noise or contamination reduction is desired, one can electronically filter out all but the moving edge shadow in a known manner, such as by a low cut off or threshold filter for detecting changing vs. fixed pixel signals, with or without a buffer. Likewise, the detection of shadow movement can be templated within a range in a speed detection register based on the feeding speed of the sheet, as also discussed above.

In either of the embodiments, the detection of the sheet edge position is not always critical, depending on the application. As described in the above and other references, for a sheet size determination, once the approximate dimension, to within, e.g., 3 mm, is known for the sheet, that approximate dimension may be compared in the controller to a look-up table to determine the nearest standard sheet dimension, e.g., in the U.S., 5", 8", 11", 14" and 17".

Various electronic and optical processing or filtering techniques and alternatives will be apparent to those skilled in the art, and need not be described herein. Note also that for both of the above embodiments, that the illumination sources need not be left on continuously. They can be turned on momentarily only when it is expected or desired to detect a sheet edge position. Also, the illumination can be non-visible light, such as IR, and/or high frequency intermittent illumination to enable frequency filtered or synchronous detection, in order to further eliminate noise or false signals from extraneous light sources.

While the embodiments disclosed herein are preferred, it will be appreciated from this teaching that various alternatives, modifications, variations or improvements therein may be made by those skilled in the art, which are intended to be encompassed by the following claims.

What is claimed is:

1. A dual mode non-contact optical sheet detection system for detecting at least one sheet edge of either fully transparent or opaque paper image substrate sheets in a sheet transport path of an image reproduction apparatus, comprising:

an illumination source for illuminating the surface of either a transparent or opaque sheet moving in said sheet transport path at a sufficiently shallow illumination angle to the surface of said sheet to generate a detectable edge shadow directly adjacent to said sheet edge from either a transparent or opaque sheet, said illumination angle being substantially greater than a grazing angle to not form shadows from said surface of said sheet.

and an optical detection system positioned to remotely detect in said sheet transport path said detectable edge shadow of said sheet without contacting said sheet, said optical detection system providing a control signal corresponding to said sheet edge passing said optical detection system, further including a spacer associated with said sheet transport path for spacing said sheet edge from said optical target area to enhance said generated edge shadow.

2. The sheet detection system of claim 1, wherein said illumination source illuminates an optical target area on one side of said sheet transport path, and said optical detection system comprises a photodetecter on the opposing side of said sheet transport path optically aimed at said target area.

3. The sheet detection system of claim 1, wherein said illumination source illuminates a sheet in said sheet transport path with said illumination angle of approximately 15 degrees to the surface of the sheet.

4. The sheet detection system of claim 2, wherein said optical target area is an optically reflective matte finish surface.

5. The sheet detection system of claim 1, wherein said optical detection system is positioned on the opposite side of said sheet transport path from said illumination source to be directly illuminated by said illumination source, and positioned to detect a lateral extent of a sheet moving orthogonally thereto in said sheet transport path.

6. The sheet detection system of claim 5, wherein said optical detection system comprises a low resolution multiple photodetector array bar positioned at one said sheet transport path for the actuation of one or more respective said photodetectors by an edge shadow of a lateral sheet edge in said sheet transport path.

7. The sheet detection system of claim 5, wherein said optical detection system comprises a low resolution photodetector array bar with an optical resolution of only approximately 3 mm or greater.

8. A dual mode non-contact optical sheet detection system for detecting at least one sheet edge of either fully transparent or opaque paper image substrate sheets in a sheet transport path of an image reproduction apparatus, comprising:

an illumination source for illuminating the surface of either a transparent or opaque sheet moving in said sheet transport path at a sufficiently shallow illumination angle to the surface of said sheet to generate a detectable edge shadow directly adjacent to said sheet edge from either a transparent or opaque sheet.

said illumination angle being substantially greater than a grazing angle to not form shadows from said surface of said sheet, and an optical detection system positioned to remotely detect in said sheet transport path said detectable edge shadow of said sheet without contacting said sheet, said optical detection system providing a control signal corresponding to said sheet edge passing said optical detection system, wherein said sheet transport path includes lifting means for lifting a sheet in said sheet transport path by approximately 1 mm relative to said optical detection system to enhance said sheet edge shadow.

* * * * *